(12) United States Patent
Schildmeyer (10) Patent No.: US 6,498,641 B1
(45) Date of Patent: Dec. 24, 2002

(54) CONDENSATION NUCLEUS COUNTER WITH MULTI-DIRECTIONAL FLUID FLOW SYSTEM

(75) Inventor: Frederic Schildmeyer, Portland, OR (US)

(73) Assignee: Pacific Scientific Instruments Company, Grants Pass, OR (US)

( * ) Notice: Subject to any disclaimer, the term of this patent is extended or adjusted under 35 U.S.C. 154(b) by 60 days.

(21) Appl. No.: 09/872,741

(22) Filed: Jun. 1, 2001

(51) Int. Cl.[7] .................................................. G01N 1/00
(52) U.S. Cl. ......................... 356/37; 356/335; 73/865.5
(58) Field of Search ........................... 356/37, 339, 338, 356/336, 335, 440, 439, 438; 73/28.01–28.06, 865.5, 863.21; 324/459, 460, 464

(56) References Cited

U.S. PATENT DOCUMENTS 5,118,959 A * 6/1992 Caldow et al. ............. 250/573

6,408,704 B1 * 6/2002 Willeke ..................... 76/865.5

* cited by examiner

*Primary Examiner*—Kevin Pyo
*Assistant Examiner*—Seung C. Sohn
(74) *Attorney, Agent, or Firm*—Stoel Rives LLP (57) ABSTRACT

A condensation nucleus counter (CNC) device implemented with a multi-directional fluid flow system is configured in a compact, conical geometry. A saturation region includes an inlet that delivers into an annular pool a sample stream of air containing small-diameter particles. The stream of air flows out and expands radially from the inlet and mixes with a working vapor to become saturated in the saturation region. The saturated fluid mixture then flows to a condensation region defined by spaced-apart inner and outer radially converging walls having a conical geometry, thereby forming an annular flow volume of decreasing cross sectional area in the direction of fluid flow to the outlet of the CNC device. The working vapor condenses on the small-diameter particles to enlarge their sizes with less tendency to condense on the inner walls of the condensation region.

17 Claims, 5 Drawing Sheets

CONDENSATION NUCLEUS COUNTER WITH MULTI-DIRECTIONAL FLUID FLOW SYSTEM

TECHNICAL FIELD

This invention relates to particle detection and, in particular, to particle detection achieved by a condensation nucleus counter that implements a multi-directional fluid flow system to enlarge condensation nuclei of submicron particles entrained in a fluid stream such that they can be detected and counted.

BACKGROUND OF THE INVENTION

The current technological trend toward the design of electronic and other devices with increasingly smaller device dimensions has created an increased need for detecting a presence of submicron diameter contaminant particles in facilities where such devices are manufactured. Such need is especially urgent in the field of microelectronic device fabrication, in which the presence of particulate contaminants results in a significant reduction in product yield.

Use of a condensation nucleus counter (CNC) represents one method of detecting the presence of submicron particles. In CNC devices, a process of diffusion thermal cooling of a fluid stream carrying submicron particles enlarges the diameters of the particles to sizes that allow their detection using conventional techniques. During thermal diffusion cooling, a submicron particle-carrying fluid sample is passed over a heated pool of volatile liquid, resulting in saturation of the fluid sample with volatile liquid vapor. The resulting vapor-fluid sample mixture is then cooled by thermal diffusion from the cold walls of a condenser. This cooling results in condensation of the vapor onto the surfaces of the submicron particles, thereby enlarging them to form droplets of sufficient size to allow optical detection of the particles.

The resolution afforded by a CNC device depends upon droplet size. Droplet size is a function of condensation time, which is dependent on the flow rate of the vapor-fluid sample mixture and the length of the flow path through the condenser. Specifically, reducing the flow rate causes maximum supersaturation to occur at a location closer to an inlet tube of the CNC device. A shorter flow path facilitates the design of a lightweight, lower cost instrument. However, reduction of the flow rate also results in increased processing time, which leads to inefficient and more costly particle detection.

Thus, a first problem encountered in prior art CNC devices is an inability to reconcile these competing benefits and detriments to arrive at a lightweight, low-cost instrument that performs efficient and cost-effective particle detection. A second problem with prior art CNC devices is that the submicron particles have a tendency to bounce off the impaction stage and become re-entrained in the flow system of CNC devices. The number of incidences of so-called "particle bounce" events increases with flow rate. One prior art method of minimizing particle bounce is described in U.S. Pat. No. 5,659,388 and entails applying grease to the impaction stage. This method is of limited utility because it introduces contaminants into the CNC device and thereby renders it unsuitable for use in many high-technology industries including microelectronic device fabrication.

What is needed, therefore, is a lightweight, low-cost CNC device implementing an improved method for efficiently and cost-effectively detecting the presence of submicron particles while limiting the incidence of particle bounce.

SUMMARY OF THE INVENTION

An object of the invention to provide a compact, lightweight CNC device that uses a multi-directional, and preferably radial, fluid flow system to enlarge condensation nuclei of submicron particles carried by a sample fluid stream for detection.

Another object of the invention is to provide such a device that forms a radially expanding fluid flow path in a working fluid saturation region to increase diffusion time of the working fluid into the sample fluid to form a saturated fluid mixture.

A further object of the invention is to provide such a device that implements a radially convergent fluid flow in a condensation region to decrease the length of the fluid flow path.

Still another object of the invention is to provide such a device that incorporates a conical geometry in the condensation region to form an annular fluid flow path of decreasing cross sectional area to increase the velocity of the sample fluid stream as it flows through the condensation region.

Yet another object of the invention is to provide such a device that operates within a range of above ambient fluid pressures to count with high resolution a greater percentage of entrained particles.

The present invention is a condensation nucleus counter (CNC) device implemented with a multi-directional, and preferably radial, fluid flow system. A preferred embodiment of the CNC device includes a saturation region and a condensation region configured in a compact, conical geometry. The saturation region includes a working fluid pool and an annular fluid pool separated by a working fluid—working vapor interface. The saturation region is heated to form from the pool of working fluid a vapor that enters the annular fluid pool. A preferred working fluid is a liquid, such as water, which evaporates to form water vapor. The saturation region includes a tubular inlet that exhausts a sample stream of air containing small-diameter particles into the annular fluid pool above a working fluid surface, which defines the working fluid—working vapor interface. The stream of air flows out radially from the inlet, expands across the working fluid surface, and mixes with the working vapor to become saturated in the saturation region. The flow velocity of the air stream slows as it expands and thereby increases the diffusion time of the working vapor to form the saturated fluid mixture.

The saturated fluid mixture then flows through an annular inlet to the condensation region and out of the CNC device through a tubular outlet. The condensation region is defined by spaced-apart inner and outer radially converging walls having a conical geometry, thereby forming an annular flow volume of decreasing cross sectional area in the direction of fluid flow from the inlet to the outlet. The working vapor condenses on the small-diameter particles to enlarge their optical scattering cross sections with less tendency to condense on the inner and outer walls of the condensation region. Thus, particles having diameters on the order of nanometers are the seeds for droplets having diameters on the order of microns.

The measurement resolution of the CNC device depends of the sizes of the particles to be detected. Particle size is a function of the fluid flow rate and the length of the flow path through the CNC device. The radial fluid flow system and conical geometry of the condensation region ensure that the residence time of the particles within the CNC device is great enough to achieve supersaturation of the particles in a compact device. An alternative embodiment receiving and processing a sample stream at above ambient pressures counts a greater percentage of particles because the higher fluid pressure contributes to a minimization of working vapor dropout onto the interior flow surfaces of the condensation region.

Additional objects and advantages of this invention will be apparent from the following detailed description of preferred embodiments thereof which proceeds with reference to the accompanying drawings.

DETAILED DESCRIPTION OF PREFERRED EMBODIMENTS

A preferred embodiment of the invention is a condensation nucleus counter (CNC) device that is commonly used to monitor and control the quality of air contained within certain environmentally controlled areas such as, for example, a clean room of a semiconductor manufacturing facility. A CNC device detects airborne particles that could cause contamination and lower the product yield of such manufacturing facilities. The airborne particles are enlarged within the CNC device by a process in which nucleation and condensation cause the airborne particles to become enlarged enough to be detected. Nucleation occurs when a sample stream of air in which the airborne particles are entrained becomes saturated with a working fluid vapor. Condensation onto the airborne particles occurs when the saturated sample stream of air reaches higher saturation or supersaturated conditions. The enlarged particles can then be detected and counted by the particle counter.

Figure 1:
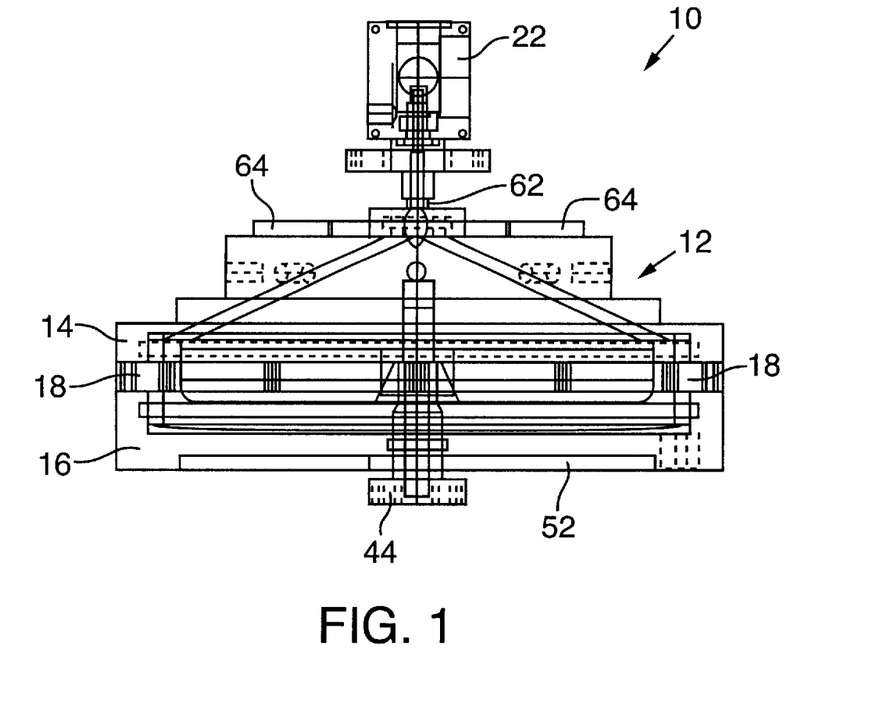
FIGS. 1, 2, and 3 are respective side elevation, top plan, and sectional views of the CNC device of the present invention.
Figure 2:
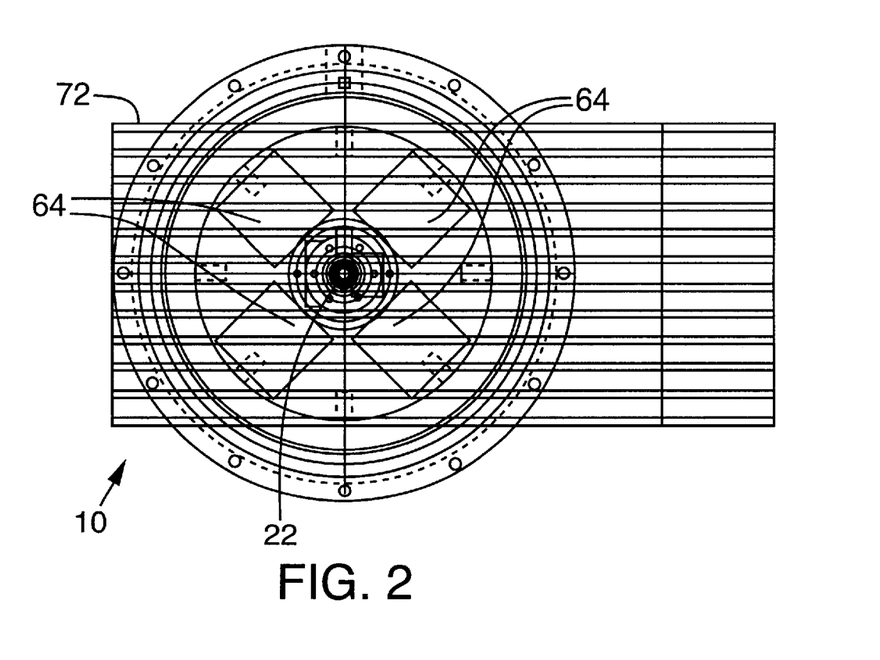
Figure 3:
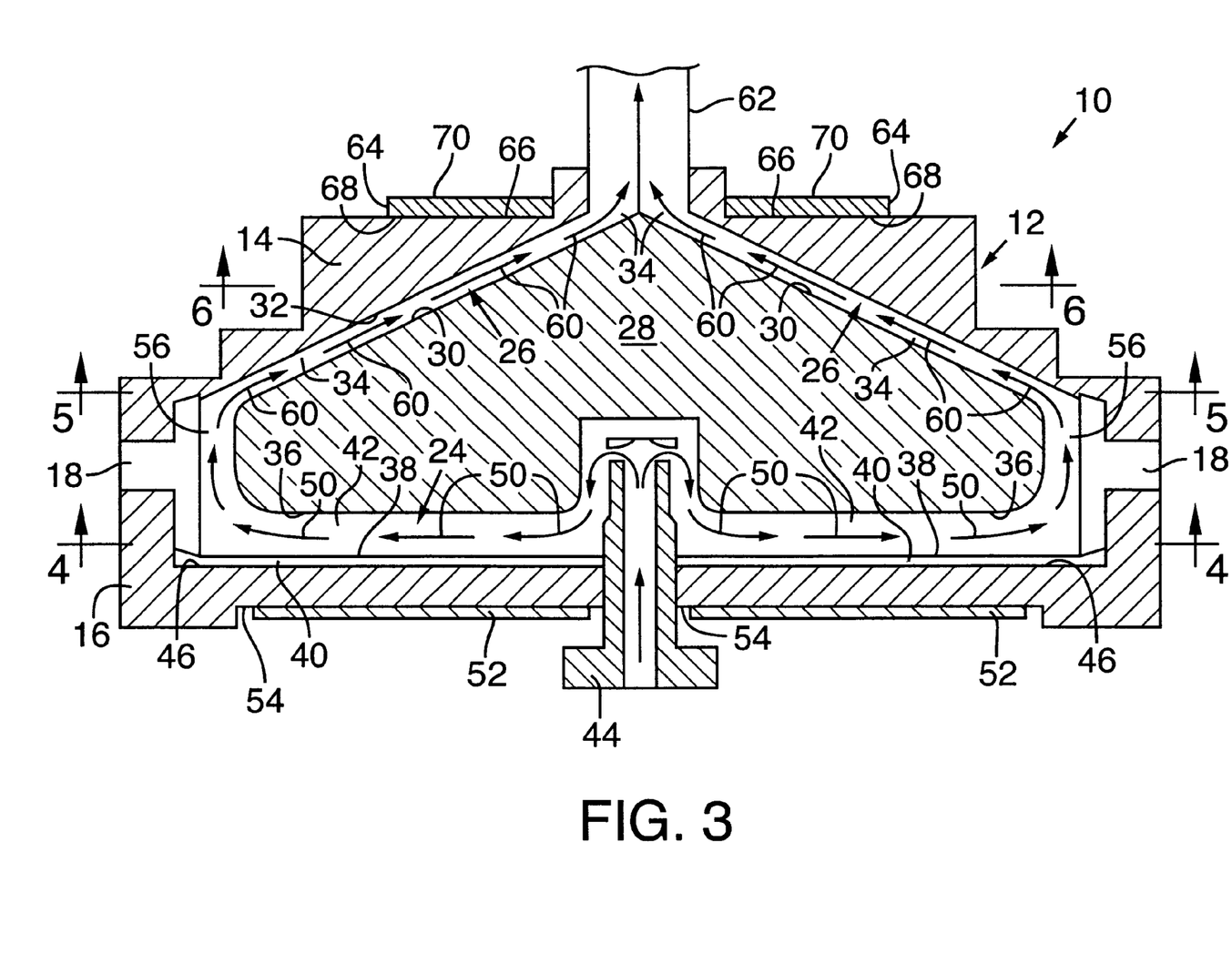

FIGS. 1, 2, and 3 show a CNC device 10 that includes a containment vessel body 12 composed of a top or condenser portion 14 and a bottom or saturator portion 16 separated by a thermally insulating gasket material 18. Top and bottom portions 14 and 16 are preferably made of 6061-T6 black anodized aluminum because of its thermal conductivity properties, and gasket material 18 is preferably made of Teflon® material because of its corrosion resistance properties. A sample fluid stream such as, for example, a sample stream of ambient air in which small-diameter particles are entrained flows to a sensor portion 22 of an optical particle counter that detects and counts a number of particles representing the concentration of small-diameter airborne particles entrained in the fluid stream. The optical particle counter is preferably of a 90° scattering detector type that is implemented without a light reflecting element. Body 12 includes a saturation region 24 and a condensation region 26 through which the sample air stream flows so that the particles entrained in the air stream become enlarged and can be more easily detected and counted by the optical particle counter. Body 12 houses a flow distributor 28 of generally conical shape. Flow distributer 28 has an outer surface upper wall 30 that together with an inner wall section 32 of top portion 14 of body 12 forms an annular fluid flow channel 34 for condensation region 26 and has an outer surface lower wall 36 that together with a top surface 38 of a working fluid pool 40 contained within lower portion 16 of body 12 forms an annular fluid pool 42 for saturation region 24.

Annular fluid pool 42 receives at its center an insulated inlet tube 44 through which the sample air stream flows at a sample air stream velocity. The sample air stream flows downwardly out of inlet tube 44 and radially throughout annular fluid pool 42, as indicated by flow direction arrows 50 in FIGS. 3 and 4. Working fluid pool 40 is held by a lower inner wall section 46 of bottom portion 16 of body 12 and contains a working liquid such as, for example, water or alcohol. Saturation region 24 is thermally conductive and preferably is heated so that the working liquid contained in working fluid pool 40 evaporates. An electric heater 52 formed in the shape of an annulus is bonded to a flat bottom surface 54 of bottom portion 16 of body 12. Heater 52 is of an electrical resistance type formed with silicone rubber-covered heater wires to which a DC voltage is applied. One such heater is a Model No. 047047 U1 47/99 manufactured by Heatron. The operating temperature of saturation region 24 is preferably about 45° C.

As described above, insulated inlet tube 44 that is centrally located in body 12 delivers the stream of sample air for radial outward expansion through annular fluid pool 42 of saturation region 24. As the working liquid contained in working fluid pool 40 evaporates, the resulting vapor saturates the stream of sample air flowing along radial fluid flow path 50 to form a saturated fluid mixture. Nucleation occurs at this point in saturation region 24 as the airborne particles in the fluid mixture become saturated with the working liquid vapor.

Figure 4:
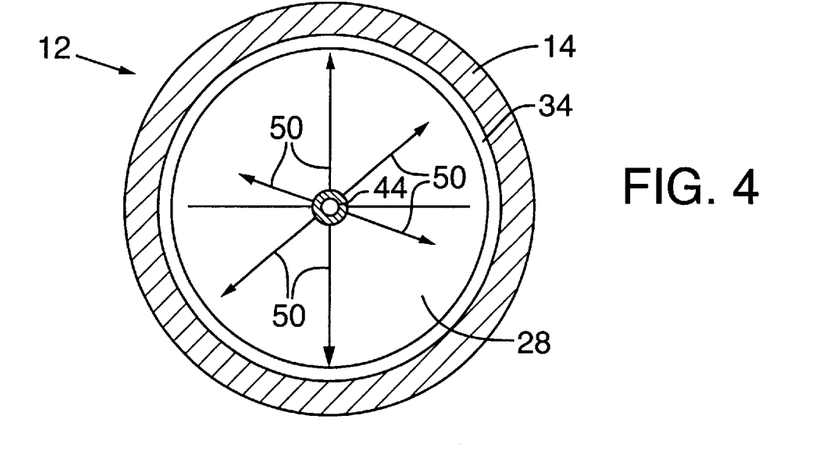
FIG. 4 is a sectional view taken along lines 4—4 of FIG. 3.
Figure 5:
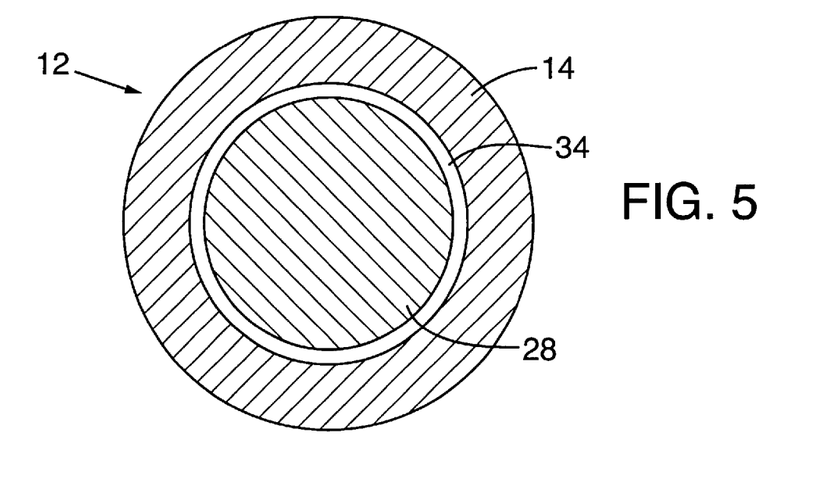
FIG. 5 is a sectional view taken along lines 5—5 of FIG. 3.
Figure 6:
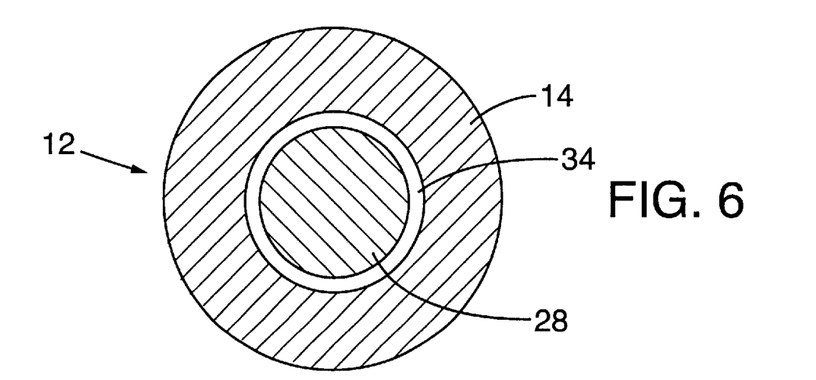
FIG. 6 is a sectional view taken along lines 6—6 of FIG. 3.

The saturated fluid mixture then flows through an annular entrance 56 to condensation region 26. Inner wall section 32 of top portion 14 of body 12 and outer surface upper wall 30 of flow distributor 28 are conically shaped and are spaced apart to define annular flow channel 34 for the saturated fluid mixture. The spacing between inner wall section 32 of body 12 and outer surface upper wall 30 of the flow distributor 28 remains substantially constant along the length of annular flow channel 34. The conical shapes of inner wall section 32 and outer surface upper wall 30 define annular flow channel 34 of decreasing cross sectional area in the direction of fluid flow through condensation region 26, as best seen in FIGS. 4–6. The direction of fluid flow is indicated by direction arrows 60 in FIG. 1. Condensation region 26 is cooled by four thermoelectric coolers 64 mounted on top portion 14 of body 12 to cause the working fluid vapor in the saturated fluid mixture to become supersaturated and condense on the airborne particles so that they expand in optical scattering cross section (i.e., size) before exiting body 12 through a tubular exit port 62 to sensor portion 22 of the optical particle counter. Thermoelectric coolers 64 are preferably spaced equidistantly around and mounted to a flat top surface 66 of top portion 14 of body 12. One such type of thermoelectric cooler 64 is a Model No. ST171-12L-1 manufactured by Mekor. In operation, each thermoelectric cooler 64 develops a heat gradient across its height dimension such that a surface 68 contacting flat top surface 16 is cold and an opposite surface 70 is hot. Surface 70 is in thermal contact with a heat sink 72 (FIGS. 2 and 8) to dissipate the heat produced. The operating temperature of condensation region 26 is preferably about 9° C. Saturation region 24 and condensation region 26 are thermally insulated from each other by insulating gasket 18 extending between confronting peripheral surfaces of top and bottom portions 14 and 16 of body 12. Flow distributor 28 is also insulated and serves to thermally separate saturation region 24 and condensation region 28.

The above-described embodiment of CNC device 10 is configured in a conical geometry with a radially expanding sample fluid stream inlet flow across a heated liquid bath in saturation region 24 followed by a radially convergent flow through a cooled annular condensation region 26. The radial expansion of the sample fluid stream reduces its velocity before the saturated fluid mixture reaches the transition to condensation region 26. Decelerating the sample fluid stream flow to a sufficient amount minimizes the dependence of the extent of working fluid saturation on the fluid flow rate. Saturation region 24 and condensation region 26 share a common volume defined by containment vessel body 12 with thermal isolation. Top portion 14 of CNC device 10 is cooled for condensation, and bottom portion 16 of CNC device 10 is heated for saturation. Temperature measuring thermistors (not shown) are positioned at various locations on the outer surface of body 12 at the hot and cold regions (and at inlet tube 44) to help regulate their temperatures. The top surface 38 of working fluid pool 40 is constant and, therefore, defines the fluid flow cross section of saturation region 24.

The radial flow system including the radial fluid flow from inlet tube 44 and the radially convergent flow in condensation region 26 provides increased residence time of the fluid mixture within a compact unit. Thus, a lengthy fluid flow path, which would normally be required to increase residence time, is avoided. The radial flow system also reduces the particle velocity within saturation region 24, allowing more residence time in saturation region 24 to ensure that the particles are adequately saturated by the vapor.

Skilled persons will appreciate that a vapor permeable membrane may be positioned at or near top surface 38 of the working fluid to provide an interface between working fluid pool 40 and annular fluid pool 42. Such a membrane could be made of, for example, Naphion material for use with an alcohol working fluid. No membrane is, however, preferably used with water as the working fluid.

An alternative use of CNC device 10 is to operate it with a sample fluid stream flowing at an elevated pressure relative to ambient external pressure. Prior art devices typically use a diffuser to reduce to ambient pressure levels the pressure of a sample fluid stream before its delivery to the inlet tube. Operating CNC device 10 at elevated pressure helps minimize dropout of water vapor onto the cold surfaces in condensation region 26 because of the reduced mobility of the water vapor and air molecules. Reducing such dropout of water vapor results in a greater percentage of detected flow particles and better uniformity of water droplet diameters, the latter providing better particle counting resolution.

The use of an elevated pressure condensation region 28 promotes condensation of the working fluid vapor onto the saturated airborne particles and allows small molecular working fluids such as, for example, water to be used without appreciable vapor depletion regions. Depletion of vapor in regions near inner wall section 32 of condensation region 28 makes difficult a 100% supersaturation of the fluid mixture. The use of an elevated pressure in condensation region 28 provides approximately 100% supersaturation of the fluid mixture using small molecular working fluids.

Although there is a measurable, insignificant pressure drop between saturation region 24 and condensation region 26, there is preferably no differential pressure purposefully introduced between them. A preferred range of sample fluid stream pressure is between about 35 psi and 135 psi, as compared with 14.7 psi, representing a typical ambient pressure, depending on the elevation.

The final diameter and nucleation threshold of the particles are depend various factors such as, for example, the operating temperatures of the saturation and condensation regions and the operating pressure in the condensation region. Saturation temperatures typically range between about 40° C. and 60° C., and condensation temperatures typically range between about 5° C. and 20° C. The final particle droplet diameters typically range between about 1 $\mu$m and 2 $\mu$m to give minimum particle detector sensitivities of between about 0.01 $\mu$m and 0.02 $\mu$m.

Figure 7:
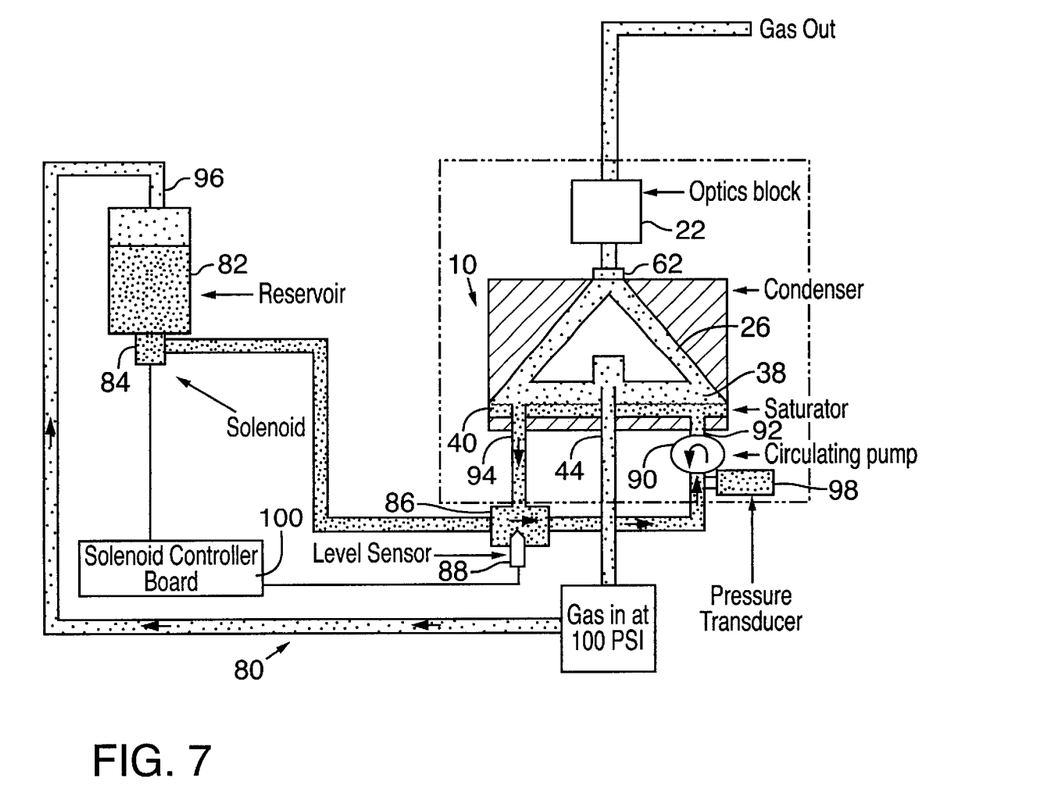
FIG. 7 is a diagram showing a fluid control system that provides a working fluid to a working fluid pool of the CNC device of FIGS. 1–3.

FIG. 7 is a diagram of a working fluid fill system 80 that provides a constant working fluid level in working fluid pool 40. The particular example depicted by FIG. 7 shows an operational configuration of working fluid fill system 80 in which CNC device 10 receives a pressurized sample gas stream. With reference to FIG. 7, a reservoir 82 holding a quantity of water, which is a preferred working fluid, has a solenoid-controlled outlet port 84 that supplies the working fluid to one port of a three-port flow valve 86 equipped to which an optical level sensor 88 is connected. The other two ports of flow valve 86 form part of a working fluid circulation flow path of working fluid that a circulating pump 90 propels through working fluid pool 40 by entry into and discharge from, respectively, an inlet port 92 and an outlet port 94.

A sample gas stream delivered at 100 psi through inlet tube 44 into annular fluid pool 42 exerts a downward pressure against the working fluid contained in working fluid pool 40. A pressure transducer 98 positioned to receive working fluid flowing out of flow valve 86 and into circulating pump 90 monitors the operating pressure inside saturation region 24 and condensation region 26. The pressurized sample gas stream is also delivered to an inlet 96 at the top of reservoir 82 to counterbalance such downward pressure exerted in working fluid pool 40. Optical level sensor 88 senses a presence of air in the working fluid flowing through flow valve 86 and thereby produces an output signal indicative of the working fluid level in working fluid pool 40. A solenoid controller 100 responds to an output signal from level sensor 88 that indicates the presence of air by opening outlet port 84 to start flow of working fluid through outlet port 84 of reservoir 82 in an amount that maintains an operational working fluid level in working fluid pool 40 as the working fluid circulates through it.

Figure 8:
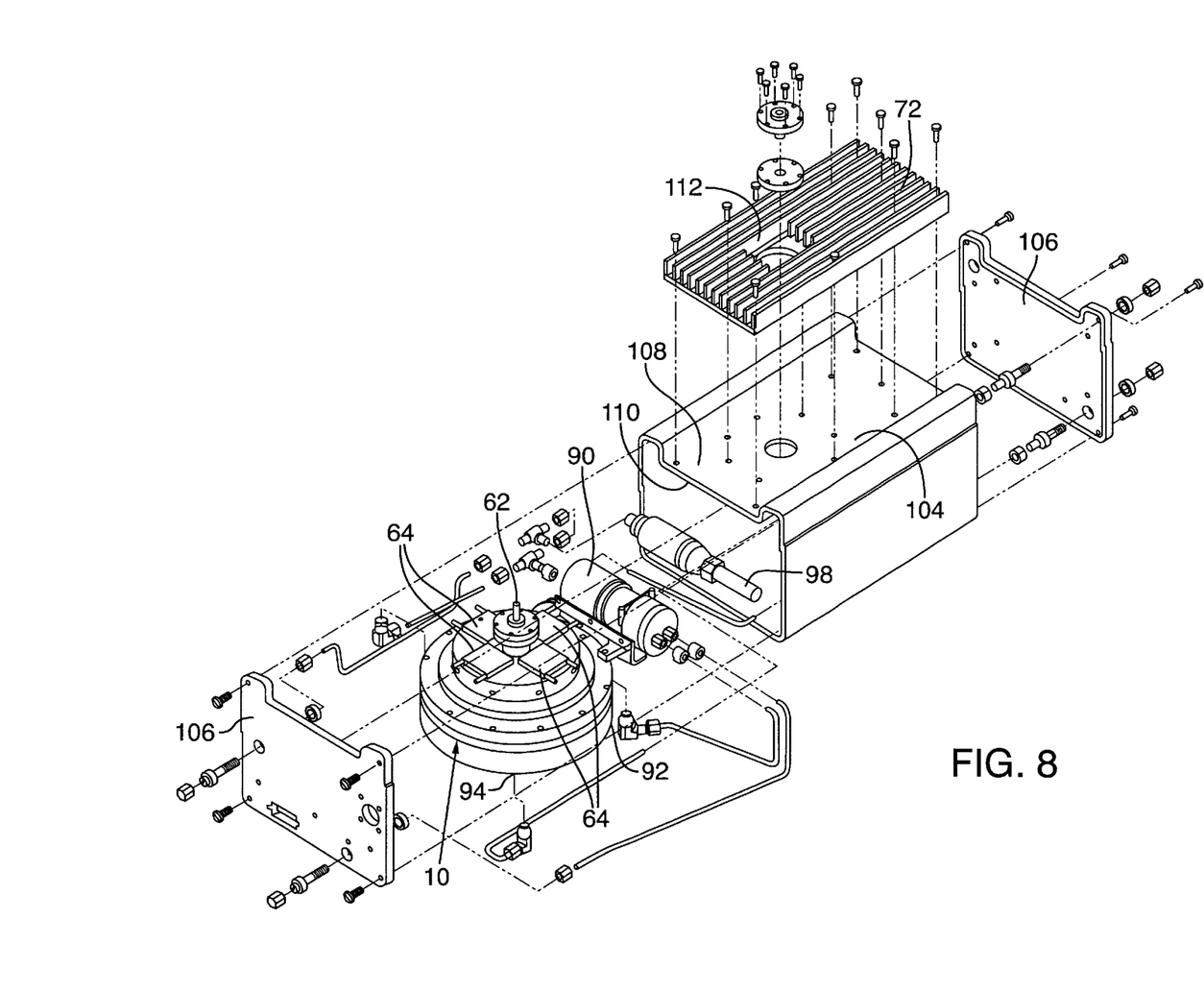
FIG. 8 is an exploded view of certain mounting fixtures and pneumatic and hydraulic components of the CNC device of FIGS. 1–3.

FIG. 8 is an exploded view of certain mounting fixtures and pneumatic and hydraulic components of CNC device 10. With reference to FIG. 8, CNC device 10, together with circulating pump 90 and pressure transducer 98, is contained by a metal housing box 104 enclosed by side cover plates 106 with apertures through which pneumatic and hydraulic fluid lines can pass. Housing box 104 includes a depression having an upper surface 108 to which heat sink 72 is mounted and a lower surface 110 against which upper surfaces 70 of thermoelectric coolers 64 are positioned for thermal conduction to heat sink 72. Sensor portion 22 of the optical particle counter projects through an opening 112 in heat sink 72 to exhaust the sample fluid stream through exit port 62.

It will be obvious to those having skill in the art that many changes may be made to the details of the above-described embodiments of this invention without departing from the underlying principles thereof. The scope of the present invention should, therefore, be determined only by the following claims.

What is claimed is:

1. A method of using a condensation nucleus counter to detect a presence of small-diameter particles entrained in a sample fluid, comprising:

introducing the sample fluid flowing at a sample fluid velocity through a sample inlet into an annular pool that is in vapor communication with a working fluid region containing a working fluid, the sample inlet emitting the sample fluid to flow at a flow velocity outwardly in multiple directions across a working fluid surface of the annular pool, the outward flow of the sample fluid expanding across the working fluid surface and thereby decreasing the flow velocity below the sample fluid velocity, the decrease in flow velocity resulting in an increase in diffusion time of working fluid vapor into the sample fluid to form a saturated fluid mixture;

directing the saturated fluid mixture from the annular pool to a condensation region having opposing inner surfaces dimensionally configured to increase the saturated fluid mixture flow to a condensation fluid flow rate;

cooling the saturated fluid mixture flowing through the condensation region to a supersaturated state that is sufficiently large to cause condensation of the working fluid vapor onto the small-diameter particles entrained in the sample fluid to enlarge their sizes; and directing to a particle detector the small diameter particles whose sizes are enlarged by the condensed working fluid vapor to detect the presence of the small-diameter particles entrained in the sample fluid.

2. The method of claim 1, further comprising applying heat to the working fluid to form the working fluid vapor, the working fluid vapor mixing with the sample fluid during the diffusion time to form the saturated fluid mixture.

3. The method of claim 1, in which the condensation nucleus counter has an exterior at an ambient pressure level, and further comprising introducing the sample fluid at a pressure higher than the ambient pressure level such that the condensation region operates at an elevated internal pressure relative to the ambient pressure level, the elevated internal pressure decreasing working fluid vapor diffusion to the cooled inner surfaces of the condensation region and thereby promoting the working fluid vapor to condense onto the entrained particles.

4. The method of claim 3, in which the working fluid comprises water.

5. A condensation nucleus counter housed in a container of compact size and characterized by low operational sensitivity to externally applied pressure, comprising:

a body including a saturation region and a condensation region positioned nearer to, respectively, an inlet end and an outlet end of the body;

the saturation region positioned near the inlet end and including an annular fluid pool and a working fluid pool, the working fluid pool having a working fluid surface that functions as an interface between the annular and working fluid pools;

an inlet member positioned at the inlet end of the body to deliver a sample fluid stream carrying small-diameter particles, the inlet member emitting the sample fluid stream in multiple directions into the annular fluid pool to form a saturated fluid mixture of the sample fluid stream and a working fluid vapor produced by evaporation of working fluid contained in the working fluid pool, the saturated fluid mixture flowing in a direction outwardly of the annular fluid pool; and the condensation region having an annular entrance end sized to receive the saturated fluid mixture as it flows out of the annular fluid pool and an exit end positioned near the outlet end of the body, and the condensation region defined by spaced apart surfaces of an inner insulating portion and an outer wall portion in the shape of an annular flow volume of decreasing cross sectional area in a fluid flow direction from the annular entrance end to the exit end, the annular flow volume being of a size that promotes condensation of the working fluid vapor onto the small diameter particles to increase their sizes before they flow through the exit end and the outlet end of the body.

6. The condensation nucleus counter of claim 5, in which the surfaces of the inner insulating and outer wall positions are spaced apart by a substantially uniform distance between the annular entrance end and exit end of the condensation region.

7. The condensation nucleus counter of claim 5, in which the inlet member emits the sample fluid stream into the annular fluid pool at a sample fluid velocity, the annular fluid pool has a cross sectional area that decreases the sample fluid velocity to a saturation flow velocity that provides a diffusion time of the working fluid vapor into the sample fluid stream to form the saturated fluid mixture, and the size of the annular flow volume causes flow of the saturated fluid mixture at a condensation flow velocity that is greater than the saturation flow velocity.

8. The condensation nucleus counter of claim 5, in which the surfaces of the insulating portion and the outer wall portion are in the general form of conical surfaces spaced apart to form the annular flow volume.

9. The condensation nucleus counter of claim 8, in which the conical surfaces are spaced apart by a substantially uniform distance between the annular entrance end and exit end of the condensation region.

10. The condensation nucleus counter of claim 5, further comprising a vapor permeable layer positioned between the annular pool and the working fluid pool.

11. The condensation nucleus counter of claim 10, in which the saturation region includes a thermally conductive surface to which heat is applied to promote formation of the working fluid vapor, the working fluid vapor penetrating the vapor permeable layer and entering the annular fluid pool.

12. The condensation nucleus counter of claim 5, in which the saturation region includes a thermally conductive surface to which heat is applied to promote formation of the working fluid vapor.

13. The condensation nucleus counter of claim 5, in which the body has an exterior at an ambient pressure level and in which the saturation and condensation regions operate at higher than ambient internal pressures such that the condensation region operates at an elevated internal pressure that decreases working fluid vapor diffusion to the surfaces of the inner insulating and outer wall portions and thereby promotes condensation of the working fluid vapor onto the small diameter particles carried by the sample fluid stream.

14. The condensation nucleus counter of claim 13, in which the elevated internal pressure ranges from between about 35 psi and about 135 psi above the ambient pressure level.

15. A method of using a condensation nucleus counter to detect a presence of small-diameter particles entrained in a sample fluid, the condensation nucleus counter having an exterior at an ambient pressure level, comprising:

introducing a sample fluid through a sample inlet into a saturation region in which a working fluid vapor diffuses into the sample fluid to form a saturated fluid mixture, the sample fluid flowing through the inlet at a pressure higher than the ambient pressure level;

directing the saturated fluid mixture from the saturator to a condensation region having cooled inner surfaces, the condensation region operating at an elevated internal pressure relative to the ambient pressure level;

cooling the saturated fluid mixture flowing through the condensation region to a supersaturated state that is sufficiently large to cause condensation of the working fluid vapor onto the small-diameter particles entrained in the sample fluid to enlarge their sizes, the elevated internal pressure decreasing working fluid vapor diffusion to the cooled inner surfaces of the condensation region and thereby promoting the working fluid vapor to condense onto the entrained particles; and directing to a particle detector the small diameter particles whose sizes are enlarged by the condensed working fluid vapor to detect the presence of the small-diameter particles entrained in the sample fluid.

16. The method of claim 15, further comprising applying heat to form the working fluid vapor, the working fluid vapor mixing with the sample fluid during diffusion to form the saturated fluid mixture.

17. The method of claim 16, in which the working fluid vapor comprises water vapor.

* * * * *